US009695216B2

(12) United States Patent
Gagnon et al.

(10) Patent No.: US 9,695,216 B2
(45) Date of Patent: Jul. 4, 2017

(54) MATERIALS AND METHODS FOR REMOVING ENDOTOXINS FROM PROTEIN PREPARATIONS

(71) Applicant: AGENCY FOR SCIENCE, TECHNOLOGY AND RESEARCH, Connexis (SG)

(72) Inventors: Peter Stanley Gagnon, Centros (SG); Vincent Vagenende, Centros (SG)

(73) Assignee: Agency for Science, Technology and Research, Singapore (SG)

( * ) Notice: Subject to any disclaimer, the term of this patent is extended or adjusted under 35 U.S.C. 154(b) by 28 days.

(21) Appl. No.: 14/769,245

(22) PCT Filed: Feb. 20, 2014

(86) PCT No.: PCT/SG2014/000071
§ 371 (c)(1),
(2) Date: Aug. 20, 2015

(87) PCT Pub. No.: WO2014/129973
PCT Pub. Date: Aug. 28, 2014

(65) Prior Publication Data
US 2016/0002290 A1    Jan. 7, 2016

Related U.S. Application Data

(60) Provisional application No. 61/768,232, filed on Feb. 22, 2013.

(51) Int. Cl.
C07K 1/36    (2006.01)
B01D 15/34   (2006.01)
B01D 15/36   (2006.01)
C07K 1/18    (2006.01)
C07K 1/30    (2006.01)
C07K 1/34    (2006.01)
B01D 15/38   (2006.01)

(52) U.S. Cl.
CPC ............... *C07K 1/36* (2013.01); *B01D 15/34* (2013.01); *B01D 15/363* (2013.01); *C07K 1/18* (2013.01); *C07K 1/30* (2013.01); *C07K 1/34* (2013.01); *B01D 15/3847* (2013.01)

(58) Field of Classification Search
None
See application file for complete search history.

(56) References Cited

FOREIGN PATENT DOCUMENTS

WO    WO 2013/180647    12/2013

OTHER PUBLICATIONS

Anspach et al., "Removal of endotoxins by affinity sorbents", Journal of Chromatography A, 711, (1995), pp. 81-92.
Chen et al. "Factors affecting endotoxin removal from recombinant therapeutic proteins by anion exchange chromatography", Protein expression and purification 64, (2009), pp. 76-81.
Clutterbuck et al., "Separation & Purification: endotoxin reduction using disposable membrance adsorption thecnolgoy in cGMP manufacturing", May 1, 2017, BioPharm International, vol. 20, Issue 5, pp. 1-6.
Cotton et al, "Lipopolysaccharide is a frequent contaminant of plasmid DNA preparation and can be toxic to primary human cells in the presence of adenovirus", Gene Therapy, vol. 1, No, 4, Jul. 1994, pp. 239-246.
Ding et al., "High performance affinity capture-removal of bacterial pyrogen form solutions", Journal of Chromatography B, 759, (2001), pp. 237-246.
Extended European Search Report dated Sep. 2, 2016 for Appln. No. 14754782.2.
Gagnon et al., "A Ceramic Hydroxyapatite-Based Purification Platform", BioProcess International, Feb. 2006, pp. 50-60.
Hou et al., "Endotoxin Removal by Anion-Exchange Polymeric Matrix", Biotechnology and applied biochemistry 12, (1990), pp. 315-324.
International Search Report dated Apr. 8, 2014 for Appln. No. PCT/SG2014/000071.
Kang et al., "Effects of ionic strength and pH on endotoxin removal efficiency and protein recovery in an affinity chromatography", Process Biochemistry 36, (2000), pp. 85-92.
Nian et al., "Void exclusion of antibodies by grafted-ligand porous particles anion exchangers", Journal of Chromatography A, 1282, (2013), pp. 127-132.
Salema et al, "Removing endotoxin from biopharmaceutical solutions", Pharmaceutical Technology Europe, vol. 21, Issue 10, Oct. 1, 2009, pp. 1-9.
Tan et al., "Differential interactions of plasmid DNA, RNA and endotoxin with immobilized and free metal ions", Journal of Chromatography A, 1141, (2007), pp. 226-234.
Vagenende et al., "Allantoin as a solid phase adsorbent for removing endotoxins", Journal of Chromatography A, 1310, (2013), pp. 15-20.
Vagenende et al., "Amide-mediated hydrogen bonding at organic crystal/water interfaces enables selective endotoxin binding with picomolar affinity", American Chemical Society, 2013, pp. 4472-4478.

*Primary Examiner* — Anand Desai
(74) *Attorney, Agent, or Firm* — Walker R. Force; Pillsbury Winthrop Shaw Pittman LLP

(57) ABSTRACT

A method includes (i) adding allantoin in a supersaturating amount to a protein preparation including a desired protein and at least one endotoxin as a contaminant, (ii) removing solids after the adding step to provide a sample for further purification by void exclusion chromatography on a packed particle bed of electropositive particles in a column, the packed particle bed having an interparticle volume, (iii) applying a sample volume to the packed particle bed, wherein the electropositive particles support void exclusion chromatography, and wherein the sample volume is not greater than the interparticle volume, and (iv) eluting a purified sample including the desired protein and a reduced amount of the endotoxin. The method is optionally carried out with only the allantoin treatment or only the void exclusion chromatography.

18 Claims, No Drawings

MATERIALS AND METHODS FOR REMOVING ENDOTOXINS FROM PROTEIN PREPARATIONS

STATEMENT OF RELATED APPLICATIONS

This application is a U.S. National Stage of PCT/SG2014/000071, filed Feb. 20, 2014, which in turn claims priority U.S. Provisional Application No. 61/768,232, filed Feb. 22, 2013, the entire contents of which are incorporated herein by reference in their entireties.

BACKGROUND

Embodiments disclosed herein relate to methods for reducing endotoxin levels in protein preparations, including unpurified, partially purified, and highly purified preparations. Endotoxins are lipopolysaccharides that originate from the cell walls of gram negative bacteria. They are ubiquitous contaminants of biological preparations, which poses a serious problem because they are broad-spectrum cytotoxins that can confound research results, give false results in diagnostic assays, and render intended therapeutic products unsafe for use. This makes it important to have effective materials and methods for their removal from the biological preparations in which they reside. Many such materials and methods have been developed. Known examples include the treatment of the preparation by anion exchange chromatography where in many cases the endotoxin binds more strongly than a desired protein in the sample (Chen, R., et al. *Protein Expression and Purification* 2009, 64, 76-81). Other known examples include hydroxyapatite chromatography (Gagnon, P., et al. *BioProcess International* 2006, 4, 50-60), immobilized metal affinity chromatography (Tan, L., et al. *Journal of Chromatography A* 2007, 1141, 226-234), affinity chromatography with immobilized histidine or polymixin B (Anspach, F., et al. *Journal of Chromatography A* 1995, 711, 81-92), affinity chromatography with immobilized polymixin B affinity chromatography with immobilized endotoxin-binding peptide derived recombinantly from *Limulus* amoebocytes (Ding, J., et al. *Journal of Chromatography B* 2001, 759, 237-246), differential extraction with the surfactant Triton X-113 (Cotten, M., et al. *Gene Therapy* 1994, 1, 239-246), and numerous proprietary commercial products and methods (Kang, Y., et al. *Process Biochemistry* 2000, 36, 85-92); Salema, V., et al. *Pharmaceutical Technology Europe* 2009, 21, 36-41); Clutterbuck, A., et al. *Biopharm International* 2007, 20, 24-31). All of these methods exploit the properties of the endotoxins' lipid-A and core polysaccharide regions, which together participate in strong hydrophobic interactions, metal affinity interactions, and/or strong electrostatic interactions with positively charged surfaces. A technique called void exclusion anion exchange has been described for IgG purification, that also reduces endotoxin content (Nian, R., et al. *J. Chromatography A* 1282 (2013) 127-132) it achieves broader utility than many previously known methods because it accommodates samples without requirement for their previous equilibration to particular chromatography conditions and its ability to achieve buffer exchange in conjunction with endotoxin removal. A technique employing supersaturated allantoin to remove endotoxin from protein preparations has been described that has the feature of tolerating a wide range of chemical conditions, including wide ranges of pH, wide ranges of salt concentration, and the presence of organic additives, including surfactants (Vagenende, V., et al. *ACS. Appl. Mater. Interfaces* 5 (2013) 4472-4478; Vagenende, V., et al. *J. Chromatography A*, 1310 (2013) 127-132).

SUMMARY

In some aspects, embodiments disclosed herein relate to methods comprising (i) adding allantoin in a supersaturating amount to a protein preparation comprising a desired protein and at least one endotoxin as a contaminant, (ii) removing solids after the adding step to provide a sample for further purification by void exclusion chromatography on a packed particle bed of electropositive particles in a column, the packed particle bed having an interparticle volume, (iii) applying a sample volume to the packed particle bed, wherein the electropositive particles support void exclusion chromatography, and wherein the sample volume is not greater than the interparticle volume, and (iv) eluting a purified sample comprising the desired protein and a reduced amount of the endotoxin, wherein the desired protein resides in the buffer to which the column was equilibrated, regardless of the buffer contents applied to the column.

In other aspects, embodiments disclosed herein relate to methods comprising (i) adding allantoin in a supersaturating amount to a protein preparation comprising a desired protein and at least one endotoxin as a contaminant, (ii) removing solids after the adding step to provide a sample comprising the desired protein and a reduced amount of the endotoxin.

In still other aspects, embodiments disclosed herein relate to methods comprising: (i) providing a protein preparation comprising a desired protein as a sample having a sample volume, the sample being suitable for void exclusion chromatography on a packed particle bed of electropositive particles in a column, wherein the electropositive particles support void exclusion chromatography, the packed particle bed having an interparticle volume, and wherein the sample volume is not greater than the interparticle volume; (ii) applying the sample to the packed particle bed, and (iii) eluting a purified sample comprising the desired protein and a reduced amount of the endotoxin.

DETAILED DESCRIPTION

In some embodiments, it has been discovered that a two-step treatment comprising incubation of an endotoxin-contaminated protein preparation comprising a desired protein with allantoin at a supersaturating concentration, followed by chromatography on packed electropositive particles in void exclusion mode provides more versatile and effective endotoxin reduction than conventional treatments. In contrast to known methods, insoluble allantoin co-precipitates endotoxin, by what is apparently hydrogen bonding. Without being bound by theory, the portions of endotoxins forming hydrogen bonds with allantoin may include the portions known as the O-antigen, the core polysaccharide, or the lipid A portion. It has been indicated that due to the reliance on hydrogen binding, the affinity of allantoin for endotoxin is not significantly affected by broad variations in pH, salt concentration, or the presence of organic solvents. The void exclusion anion exchange step may bind the core polysaccharide and lipid-A regions of endotoxin. The combination of allantoin affinity and void exclusion step thereby potentially targets all regions of the endotoxin molecule, which likely accounts for the high endotoxin removal efficiency of the dual treatment system. The combination of methods also overcomes a potential shortcoming of endotoxin removal by allantoin, which is that the treated sample contains soluble residual allantoin and may contain other components, including salts and organic additives, which may interfere with the application of the reduced-endotoxin sample. Since the void exclusion step supports the simultaneous function of buffer exchange, and its efficacy is unaffected by the pH, conductivity, or other properties of the protein preparation applied to it, the allantoin-treated sample, following removal of solids, can be conveniently applied directly to the void exclusion column, from which it elutes in the buffer to which the column was equilibrated, and which buffer may be formulated to match the requirements of the intended application of the endotoxin depleted protein. In many cases, the void exclusion step provides the additional benefit of achieving a high degree of purification of the desired protein. The primary role of the void exclusion step however remains to augment the endotoxin reduction factor achieved by allantoin. In some cases, allantoin removes endotoxin more effectively than void exclusion; in some cases the pattern is reversed, but in all cases observed to date, the combination removes more than either alone, in addition the other benefits noted above.

Thus, in some embodiments, there is provided a method comprising (i) adding allantoin in a supersaturating amount to a protein preparation comprising a desired protein and at least one endotoxin as a contaminant, (ii) removing solids after the adding step to provide a sample for further purification by void exclusion anion exchange chromatography, (iii) applying a sample volume to a packed bed of electropositive particles, wherein the electropositive media supports void exclusion chromatography, wherein the sample volume is not greater than an interparticle volume of the packed particle bed, and (iv) eluting a purified sample comprising the desired protein and a reduced amount of the endotoxin. This two phase process employing allantoin followed by void exclusion chromatography may provide the desired protein with greater, than about 99% removal of endotoxins, in other embodiments, greater than about 99.5%, in other embodiments, greater than about 99.99%. In some embodiments, the method may provide the desired protein with no observable endotoxin impurities up to the limits of detection.

In some embodiments, the supersaturating amount of allantoin comprises an amount selected from the group consisting of: (i) about 10%, (ii) about 5%, (ii) from about 0.6 to about 6%, (iii) from about 6% to about 10%, (iv) from about 10% to about 15%, (v) from about 15 to about 20%, and (vi) greater than 20%, wherein the amount is provided as weight/volume. One skilled in the art will appreciate that each of the recited amounts and ranges all constitute a supersaturating amount of allantoin. In some embodiments, a supersaturated amount may include an amount of undissolved allantoin.

In some embodiments, removing the solids comprises one selected from the group consisting of centrifugation, filtration, and combinations thereof. These and other methods for removing solids are well known by those skilled in the art. Filtration may include vacuum, or gravity, or pump-impelled filtration of any scale required to process samples of the required volume.

In some embodiments, a pH or salt concentration of the protein preparation may be adjusted before, during, or after the adding step.

In some embodiments, a pH or salt concentration of the protein preparation may be adjusted before the applying step.

In some embodiments, the applied sample volume does not exceed a particle volume of the packed particle bed. In some embodiments, the sample volume is less than the interparticle volume of the packed particle bed by an amount comprising one selected from the group consisting of: (i) less than about 40%, (ii) less than about 35% of the bed volume, (iii) less than about 30% of the bed volume, (iv) less than about 20% of the bed volume, (v) less than about 10% of the bed volume, (vi) less than about 5% of the bed volume, (vii) less than about 2% of the bed volume, and (viii) less than about 1% of the bed volume. In some embodiments, the sample volume may be less than about 40% of the bed volume. In particular embodiments, it may be beneficial to apply the largest possible sample volume while still staying within a range suitable for void exclusion chromatography since they will support the greatest volumetric capacity per iteration. In other particular embodiments, it may be beneficial to apply a sample volume of about 35% of the bed volume. While a greater sample may be useable, a volume of about 35% may provide a practical margin of safety for operational errors compared to working closer to the theoretical limit, where such errors could prevent the methods from achieving its greatest benefits. For this reason, in some embodiments, a kit is provided, the operating instructions of which may advantageously recite sample volumes of about 35% of the bed volume, thus providing a buffer against possible operating error.

In some embodiments, before the applying step, the method further comprises equilibrating the packed particle bed of anion exchange media with a buffer selected to prevent the desired protein from substantially binding to the anion exchange media. In some such embodiments, preventing the desired protein from substantially binding to the electropositive media comprises providing the buffer with a sufficiently low pH. In some such embodiments, preventing the desired protein from substantially binding to the electropositive media comprises providing the buffer with a sufficiently high salt concentration.

Thus, in some embodiments, the buffer may have a pH comprising one selected from the group consisting of (i) about 7, (ii) about 8, (iii) about 6, and (iv) a range from about 6 to about 8. One skilled in the art will appreciate that the operating may be higher, lower, or any intermediate value and that the exact conditions will be determined on a case by case basis through routine optimization for a particular desired protein. Thus, the values given here represent only initial guidelines for preliminary operating conditions for typical desired proteins. For example, in particular embodiments, the pH can include higher values such as, 9, 10, 11, 12, and so on. Likewise, in particular embodiments, the pH can include lower values such as 5, 4, 3, and so on. In some embodiments, the salt concentration may affect the suitable range of pH, and the converse may hold that pH may affect the suitable range of salt concentration.

In some embodiments, the buffer comprises a sodium chloride concentration comprising one selected from the group consisting of (i) about 0 mM, (ii) about 50 mM, (iii) about 150 mM, and (iv) a range from about 0 mM to about 150 mM. Again, those skilled in the art will recognize that a higher or intermediate concentration may achieve the desired result, depending on the properties of the particular desired protein being purified. In some embodiments, 0 mM sodium chloride, that is, no sodium chloride may be sufficient and, in some embodiments, optimal for a particular desired protein.

In some embodiments, the composition of the equilibration buffer, formulated first to prevent binding the desired protein, may be further formulated to favor the highest degree of endotoxin binding to maximize the ability of the disclosed methods as a whole to reduce endotoxin. In some such embodiments, as a general matter, the void exclusion equilibration conditions will generally embody some combination of the highest pH and lowest conductivity that do not cause the desired protein to bind to the chromatography media, and which do not damage the desired protein. Experimental data with one IgG monoclonal antibody, for example, have shown the best endotoxin reduction with a buffer formulation consisting of 50 mM Tris, pH 8.2. As a general matter, the priorities in developing a buffer formulation for the void exclusion step, in order, are to determine the conditions that do not cause binding of the desired protein, determine the combination of highest pH and lowest conductivity, and determine the conditions most suitable for performing the intended application of the endotoxin-deficient treated sample.

In some embodiments, electropositive chromatography media employed in the void exclusion chromatography mode comprises one selected from the group consisting of UNOsphere Q, Nuvia Q, Capto Q, Capto adhere, and other electropositive particle based media suitable for practicing the method. In some embodiments, any anion exchange media having electropositive groups may serve, however, those skilled in the art will appreciate that not all electropositive media are equally suitable. While the exact parameters that define a successful medium have not been fully elucidated, those skilled in the art can readily screen any particular electropositive media for its ability to perform void exclusion anion exchange chromatography. In some embodiments, this may be accomplished in a simple experiment where candidate anion exchange (or electropositive) particles are packed in a column, for example with a volume of about 20 mL. The particles are ideally allowed to settle by gravity, then a flow adaptor is set so that it contacts but does not significantly compress the bed. The technique may be performed on columns in which the bed has been compressed, but compression reduces the interparticle space with the direct result of reducing the volumetric sample capacity of the column. For example, a 20 mL gravity-settled bed may have a sample volume capacity as high as about 8 mL, but 25% compression of the bed to a volume of 15 mL, will reduce the capacity to a level lower than the capacity of 15 mL of the same media in a gravity-settled bed. Thus, it is believed that compression disproportionately reduces the interparticle volume, as opposed to the particle volume. The chromatography system on which the column resides is also important to successful performance of void exclusion chromatography, and is ideally configured in a way to deliver sample in a manner that does not cause significant dilution of the sample on the way to the column, since the technique depends on the volume of the sample entering the column being no greater than the interparticle volume of the column. Laminar flow is well known to dilute sample at the boundaries. In an example of a 5 mL sample loop with a length of a few meters, the volume of sample as it enters the column may be substantially greater than the 5 mL initially introduced into the loop, for example possibly increasing to 7.5 mL or even 10 mL or more. Systems with a so-called superloop are well suited for practicing the methods, because by means of their reliance on a cylinder-plunger design they permit the application of large sample volumes without the imposition of excessive dilution through laminar flow. It will be understood by persons of ordinary skill in the art that any given chromatography system also imposes a certain amount of sample dilution between the sample-introducing device (injector) and the column as a result of fluid passing through various valves and mixers, and that as a general matter, the larger the ratio of the column volume to a particular system's internal pre-column dilution volume, the lower the relative increase in at-the-column sample volume as a function system dilution. In practical terms, this means that operating a small column on a chromatograph designed and configured for large scale use will impose secondary restrictions on the volume of sample that can be applied at the injector, while operating a large column on such a system will permit the user to apply samples of greater volume that remain within the volumetric limits of a given column at the point where the sample enters the column. With the 20 mL gravity packed uncompressed column on a system such as an AKTA Explorer 100 using the dark green peek tubing, and equipped with a superloop that has been previously loaded with sample containing an IgG monoclonal antibody, and with the column equilibrated with 50 mM Tris, 50 mM NaCl, pH 8.0, a 1 mL sample is loaded to the column. A chart mark is made at the point where the antibody the antibody begins to exit from the column. Another chart mark is made at the point where the conductivity changes, indicating the passage of small molecules associated with the sample. The volume between the marks provides a serviceable estimate of the interparticle volume of the column. The ratio of the interparticle volume to the total column volume is calculated. Anion exchange chromatography media suited for performing the technique of void exclusion anion exchange chromatography will exhibit a ratio of about 1/2.5, but media exhibiting lower ratios, such as 1/2.4, 1/2.3, 1/2.2, 1/2.1, 1/2.0, or lower can provide useful results so long as the volume of the sample entering the column does not exceed the adjusted volume adjusted according to the above results.

Evaluations to date have particularly identified UNOsphere Q, Nuvia Q, Capto Q, and Capto adhere as media suitable for practicing void exclusion anion exchange chromatography. It is to be understood that the conditions suggested herein for determining the suitability of a given anion exchange medium for conducting void exclusion anion exchange chromatography with an IgG monoclonal antibody are not necessarily the conditions to achieve the most effective endotoxin removal, nor necessarily the conditions most suitable for another protein species. It is to be further understood that electropositive media that include additional chemical functionalities that cause them to be marketed for so-called multimodal chromatography will require an additional dimension of process development involving evaluation of different buffer conditions to determine if that given medium is suitable for performing adsorption chromatography in void exclusion mode. One example includes the so called mixed-mode or multimodal electropositive chromatography medium marketed under the commercial name of Capto adhere, which is purported to incorporate functional groups that cause it to participate in hydrogen bonds and hydrophobic interactions. Whereas some products marketed as anion exchangers support void exclusion of IgG monoclonal antibodies in the absence of a salt such as sodium chloride at a pH of 8.0, the additional functionalities of Capto adhere make it necessary to reduce the operating pH to about 5.0 for the medium to function in void exclusion mode. It will be understood that the reduction of operating pH has the effect of increasing the electropositivity of the antibody being processed with the effect of increasing its repellency to the electropositivity of the media, with the further effect of overcoming hydrophobic interactions and hydrogen bonding. It will be equally understood that reducing the pH to such a value will not appreciably reduce the negative charge on endotoxin phosphoryl residues by which the endotoxin is attracted to the electropositivity of the chromatography particles, so that the net effect of using such chromatography particles that embody additional secondary functionalities is that it potentially offers more effective endotoxin removal than electropositive media lacking the additional functionalities.

In some embodiments, void exclusion anion exchange chromatography may be performed at a linear flow rate comprising a non-zero linear flow rate selected from the group consisting of (i) about 300 cm/hr or less, (ii) about 200 cm/hr or less, (iii) about 100 cm/hr or less, and (iv) about 50 cm/hr or less. In some embodiments, for example where flow is induced by gravity, the ability to control flow rate is lost but endotoxin removal efficiency will be generally unaffected.

In some embodiments, methods disclosed herein may comprise contacting the sample with a soluble organic modulator selected from the group consisting of nonionic organic polymers, organic solvents, surfactants, and ureides, prior to the adding step, and/or prior to the applying step.

In some embodiments, the soluble organic modulator may be a nonionic organic polymer selected from the group consisting of polyethylene glycol, polypropylene glycol and polybutylene glycol. In some such embodiments, the nonionic organic polymer may have an average molecular weight of approximately 500 Daltons or less.

In some embodiments, the soluble organic modulator may be an organic solvent selected from the group consisting of ethylene glycol, propylene glycol, butylene glycol, dimethylsulfoxide, ethanol, isopropanol, and phenoxyethanol.

In some embodiments, the soluble organic modulator is provided at a concentration of approximately 1% (w/v) or greater.

In some embodiments, the soluble organic modulator may be a surfactant selected from the group consisting of Tween, Triton, CHAPS, CHAPSO and octyl glucoside. In some such embodiments, the surfactant may be provided at a concentration of approximately 1% (w/v) or less. In other embodiments, the surfactant may be provided at a concentration of approximately 0.1% (w/v) or less.

In some embodiments, the organic modulator may be a ureide provided in a sub saturating amount. In some such embodiments, the ureide comprises one selected from the group consisting of urea and hydantoin.

In some embodiments, there is provided a method comprising (i) adding allantoin in a supersaturating amount to a protein preparation comprising a desired protein and at least one endotoxin as a contaminant, (ii) removing solids after the adding step to provide a sample comprising the desired protein and a reduced amount of the endotoxin. In such embodiments, the desired protein may be sufficiently free of endotoxin such that the limit of detection is already achieved obviating the need for subsequent void exclusion electropositive chromatography to the extent of endotoxin removal. A follow-on void exclusion step may nevertheless offer the additional value of removing soluble allantoin and other sample components, and achieving a degree of purification that allantoin treatment alone cannot achieve. This may be particularly the case with IgG monoclonal antibodies where the technique of void exclusion anion exchange chromatography may support 99% elimination of contaminating host proteins and DNA, in addition to removing endotoxin.

In some embodiments, there is provided a method comprising (i) providing a protein preparation comprising a desired protein and at least one endotoxin as a contaminant as a sample having a sample volume, (ii) applying the sample volume to a packed particle bed of anion exchange media, wherein the anion exchange media supports void exclusion chromatography, and wherein the sample volume is not greater than the interparticle volume of the packed particle bed, and (iii) eluting a purified sample comprising the desired protein and a reduced amount of the endotoxin. In some such embodiments, the desired protein may be sufficiently free of endotoxin such that the limit of detection is achieved solely by void exclusion anion exchange chromatography obviating the need for pre-treatment with allantoin. In some such embodiments where void exclusion chromatography alone does not achieve the desired degree of endotoxin reduction, it may be followed by treatment with allantoin.

In some embodiments, there are provided kits configured for the convenient practice of any of the methods disclosed herein. Such a kit may be equipped with reagents to carry out allantoin treatment and subsequent void electropositive chromatography along with instructions.

The following non-limiting example illustrates the basic features and practice of the methods. To a convenient volume of an endotoxin-contaminated protein preparation containing a desired protein, allantoin is added in an amount of 10%, weight to volume (w/v). The sample is mixed briefly and solids are allowed to settle. Endotoxin is bound to the solids and thereby removed from the fluid. Settling may be accelerated by centrifugation. The fluid with reduced endotoxin content is decanted or filtered to remove remaining solids. The sample is applied to an electropositive void exclusion medium in an amount of 40% or less than the column volume. In the case where the desired protein in the protein preparation might be an IgG monoclonal antibody, the electropositive void exclusion column might be equilibrated with a buffer such as 50 mM Tris, pH 8.0, in which the IgG will elute with lower level of endotoxin contamination than the allantoin-treated sample in which it was applied. Experience to date indicates that 1,000-10,000 fold reduction of endotoxin content can be achieved in conjunction with 90-99% recovery of the desired protein. In the case of alkaline proteins including IgG, lysozyme, and ribonuclease, among others, the protein will also be substantially purified by the disclosed methods. Experimental data indicate that the technique can achieve 99% reduction of non-antibody proteins independent of endotoxin removal. The methods disclosed herein are easily configured as kits to increase its overall convenience.

In one embodiment, the protein preparation to be treated is a biological solution that contains a species of desired protein contaminated with endotoxin.

In one or more of the previous embodiments, the protein preparation contaminated with endotoxin comprises a cell-containing cell culture harvest.

In one or more of the previous embodiments, the protein preparation contaminated with endotoxin comprises a cell culture supernatant.

In one or more of the previous embodiments, the protein preparation contaminated with endotoxin comprises a body fluid from a human or an animal.

In one or more of the previous embodiments, the protein preparation contaminated with endotoxin comprises a cellular fluid from an organism or from a plurality of organisms of a particular species.

In one or more of the previous embodiments, the protein preparation contaminated with endotoxin comprises a homogenate of a biological tissue.

In one or more of the previous embodiments, the protein preparation contaminated with endotoxin comprises is a partially purified protein.

In one or more of the previous embodiments, the protein preparation contaminated with endotoxin comprises is a highly purified protein.

In one or more the previous embodiments, the desired protein is an antibody, or an antibody fragment such as an Fab, and F(ab')2, a ScFv, a VHH, a minibody, a diabody, or a recombinant derivative of an antibody fragment such as and Fc-fusion protein.

In one or more of the previous embodiments, the desired protein is a complement protein.

In one or more of the previous embodiments the desired protein is a clotting protein. In one such embodiment, the desired protein is Factor VIII, or a complex of Factor VIII with von Willebrand factor.

In one or more of the previous embodiments, the protein preparation to be treated is at a pH of 4, or 5, or 6, or 7, or 8 or 9, or a lower, higher, or intermediate pH value, and requires no modification of pH to perform the allantoin affinity step, the electropositive void exclusion step.

In one or more of the previous embodiments, the pH of the protein preparation may be adjusted to a particular pH.

In one or more of the previous antibodies, the protein preparation to be treated is at a contains a chaotroic (protein-solubilizing) salt, such as guanidine, or isothiocyanate; or a neutral salt such as sodium acetate, or sodium chloride; or a kosmotropic (protein-precipitating) salt such as ammonium sulfate, sodium citrate, or potassium phosphate, and requires neither the removal or addition or removal of any salt to perform the allantoin affinity step, the electropositive void exclusion step.

In one or more of the previous embodiments, the protein preparation to be treated contains a salt at a concentration of 0.1 M, or 0.2 M, or 0.4 M, or 0.8 M, or 1.6 M, or 3.2 M, or a lower, higher, or intermediate concentration, and requires neither the removal or addition or removal of any salt to perform the allantoin affinity step, the electropositive void exclusion step.

In one or more of the previous embodiments, one or more species of salt may be added to the protein preparation.

In one or more of the previous embodiments, the salt concentration of the protein preparation may be reduced, for example by dilution with a liquid containing a lesser concentration of salt or a liquid lacking salt.

In one or more of the previous embodiments, the protein preparation to be treated contains a nonionic chaotrope such as urea at a concentration of 0.5 M, or 1.0 M, or 2.0 M, or 4.0 M, or 8.0 M, or a lower, higher, or intermediate concentration, and requires neither the removal nor addition of any such chaotrope to perform the allantoin affinity step, the electropositive void exclusion step.

In one or more of the previous embodiments, the protein preparation to be treated contains an organic solvent such ethanol, isopropanol, ethylene glycol, propylene glycol, polyethylene glycol, polypropylene glycol, or glycerol at a concentration ranging from 1-25%, or a lower, higher, or intermediate concentration, and requires neither the presence, absence, removal or addition of any such organic solvent to perform the allantoin affinity step, the electropositive void exclusion step.

In one or more of the previous antibodies, the protein preparation to be treated contains a cationic, nonionic, zwitterionic, or anionic surfactant at a concentration of 0.01 to 1% or a lower, higher, or intermediate concentration, and requires neither the removal or addition of any such surfactant to perform the allantoin affinity step, the electropositive void exclusion step.

In one or more of the previous embodiments, allantoin is added to the protein preparation to a final concentration of 10%, or 9%, or 8%, or 7%, or 6%, or 5%, or concentration as low as 0.6%, or higher than 10%, or an intermediate value.

In one or more of the previous embodiments, the ability of the allantoin affinity step to reduce the concentration of endotoxins may be enhanced by the addition of organic multivalent ions.

In one or more of the previous embodiments, solid materials are removed from the sample before the protein preparation is applied to the electropositive void exclusion step.

In one or more of the previous embodiments, the volume of the electropositive void exclusion column is 2.5 times greater than the volume of the protein preparation sample applied to it, or 3 times greater, or 4, 5, 10, 20, 50 or more times greater than the volume of the sample applied to it.

In one or more of the previous embodiments, the volume sample applied to the electropositive void exclusion column is 40% or less than the column volume, or 30% or less, or 20% or less, or 10% or less, or 5% or less, or 1% or less than the column volume.

In some embodiments, there are provided methods comprising: (i) adding allantoin in a supersaturating amount to a protein preparation comprising a desired protein and at least one endotoxin as a contaminant; (ii) removing solids after the adding step to provide a sample for further purification by void exclusion chromatography on a packed particle bed of electropositive particles in a column, the packed particle bed having an interparticle volume; (iii) applying a sample volume to the packed particle bed, wherein the electropositive particles support void exclusion chromatography, and wherein the sample volume is not greater than the interparticle volume, and (iv) eluting a purified sample comprising the desired protein and a reduced amount of the endotoxin, wherein the desired protein resides in the buffer to which the column was equilibrated, independently from the buffer content applied to the column. Thus, methods disclosed herein effectively provide a means of buffer exchange for the desired protein into a buffer. Such buffers may be selected for appropriate follow-on assays or processing steps. Thus, the initial buffer formulation the desired protein was in when it initially contacted the column is of no consequence. This exchange highlights one of the advantages of the methods disclosed herein. By contrast, other endotoxin removal methods do not confer this ability.

In some embodiments, the supersaturating amount of allantoin comprises an amount selected from the group consisting of: (i) about 10%, (ii) about 5%, (ii) from about 0.6 to about 6%, (iii) from about 6% to about 10%, (iv) from about 10% to about 15%, (v) from about 15 to about 20%, (vi) from about 20 to about 50%, and (vii) greater than 50%, wherein the amount is provided as weight/volume.

In some embodiments, removing the solids comprises one selected from the group consisting of sedimentation, centrifugation, filtration, and combinations thereof.

In some embodiments, a pH or salt concentration of the protein preparation is adjusted before, during, or after the adding step. In some such embodiments, adjustments are not necessary, and the methods may benefit from obviating the need to perform such adjustments.

In some embodiments, a pH or salt concentration of the protein preparation is adjusted before the applying step. In some embodiments, such adjustments are not necessary, and the methods may benefit from obviating the need to perform such adjustments.

In some embodiments, the sample volume is less than the interparticle volume of the packed particle bed such that the sample volume relative to the packed bed is one selected from the group consisting of: (i) less than about 35%, (ii) less than about 30%, (iii) less than about 20%, (iv) less than about 10%, (v) less than about 5%, (vi) less than about 2%, and (vii) less than about 1%.

In some embodiments, the sample volume applied to the bed is less than the interparticle volume by an increment consisting of one selected from the group: 99% of the interparticle volume, 95% of the interparticle volume, 90% of the interparticle volume, 80% of the interparticle volume, 70% of the interparticle volume, 60% of the interparticle volume, 50% of the interparticle volume, 25% of the interparticle volume, 10% of the interparticle volume, 5% of the interparticle volume, 2% of the interparticle volume, 1% of the interparticle volume, and intermediate volume percent thereof.

In some embodiments, before the applying step, the method further comprises equilibrating the packed particle bed of anion exchange media with a buffer selected to prevent the desired protein from substantially binding to the anion exchange media.

In some embodiments, preventing the desired protein from substantially binding to the anion exchange media comprises providing the buffer with a sufficiently low pH.

In some embodiments, preventing the desired protein from substantially binding to the anion exchange media comprises providing the buffer with a sufficiently high salt concentration.

In some embodiments, the buffer has a pH comprising one selected from the group consisting of (i) about 7, (ii) about 8, (iii) about 6, and (iv) a range from about 6 to about 8. In some embodiments, pH is in a range comprising one selected from the group consisting of (i) from a pH of about 4 to a pH of about 10, (ii) from a pH of about 5 to a pH of about 9, (iii) from a pH of about 6 to a pH of about 8, (iv) from a pH of about 6.5 to about 7.5, and (v) an intermediate range.

In some embodiments, the buffer comprises a sodium chloride concentration comprising one selected from the group consisting of (i) about 0 mM, (ii) about 50 mM, (iii) about 150 mM, and (iv) a range from about 0 mM to about 150 mM. In some embodiments, a conductivity value corresponding to an NaCl concentration not greater than 150 mM may be employed. In some embodiments, conductivity may be in a range comprising one selected from the group consisting of (i) from a non-zero value to about 50 mS/cm, (ii) from a non-sero value to about 25 mS/cm, (iii) from a non-zero value to about 10 mS/cm, (iv) from a non-sero value to about 5 mS/cm, (v) from a non-zero value to about 2 mS/cm, (vi) from a non-zero value to about 1 mS/cm, and (vii) from a non-zero value to about 0.1 mS/cm. In some embodiments, a corresponding NaCl concentration may be in a range comprising one selected from the group consisting of (i) from a non-zero value to about 500 mM, (ii) from a non-zero value to about 250 mM, (iii) from a non-zero value to about 100 mM, (iv) from a non-zero value to about 50 mM, (v) from a non-zero value to about 20 mM, (vi) from a non-zero value to about 10 mM, and (vii) from a non-zero value to about 1 mM.

In some embodiments, anion exchange chromatography media employed in the void exclusion anion exchange chromatography comprises one selected from the group consisting of UNOsphere Q, Nuvia Q, or Capto Q, and another void exclusion anion exchange chromatography-capable anion exchange medium.

In some embodiments, void exclusion anion exchange chromatography is performed at a linear flow rate comprising a non-zero linear flow rate selected from the group consisting of (i) about 300 cm/hr or less, (ii) about 200 cm/hr or less, (iii) about 100 cm/hr or less, and (iv) about 50 cm/hr or less.

In some embodiments, there are provided methods comprising: (i) providing a protein preparation comprising a desired protein as a sample having a sample volume, the sample being suitable for void exclusion chromatography on a packed particle bed of electropositive particles in a column, wherein the electropositive particles support void exclusion chromatography, the packed particle bed having an interparticle volume, and wherein the sample volume is not greater than the interparticle volume; (ii) applying the sample to the packed particle bed, and (iii) eluting a purified sample comprising the desired protein and a reduced amount of the endotoxin.

In some embodiments, there are provided kits configured for the convenient practice of the methods disclosed herein. Such kits may include reagents, instructions, as necessary to the practice of the methods disclosed herein.

Terms are defined so that the methods may be understood more readily. Additional definitions are set forth throughout the detailed description.

"Interparticle volume," or "Interparticle bed volume," or "Void volume" are terms referring to the cumulative space between particles in a packed bed of particles, especially including a column packed with particles to perform chromatography. On average, the interparticle volume of a chromatography column packed with uniform spherical polymeric microparticles is about 40% of the total bed volume, where total bed volume consists of the cumulative particle volume plus the cumulative interparticle volume. Interparticle volume of a packed bed may be larger than 40% if the particles are irregular, or comprise a wide range of particle sizes, or are incompressible due to their composition. Interparticle volume may be smaller than 40% if the particle bed is compressed. The interparticle volume of a column may accordingly range from less than 30% to more than 60% of the total bed volume.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Host contaminant" or "Host cell contaminant" refers to biomolecules that are produced by the cells in which the product of interest is grown. The term may include various classes of host contaminants, such as host proteins and host DNA.

"Host protein" or "Host cell protein" or "HCP" refers to proteins that are produced by the cells in which the product of interest is grown. Such proteins represent one class of contaminants that must be removed from the product of interest.

"Antibody" refers to an immunoglobulin of the class IgG, IgM, IgA, IgD, or IgE derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety, or immunoconjugates created by synthetic linkage of an IgG to another functional moiety, including another antibody, an enzyme, a fluorphore or other signal generating moiety, biotin, a drug, or other functional moiety.

"Endotoxin" refers to a toxic heat-stable lipopolysaccharide substance present in the outer membrane of gram-negative bacteria that is released from the cell upon lysis. Endotoxins can be generally acidic due to their high content of phosphate and carboxyl residues associated with the core polysaccharide, and can be highly hydrophobic due to the fatty acid content of the lipid-A region. The O-antigen region comprises large numbers of nonionic polysaccharides.

"Non-ionic organic polymer" refers to a naturally occurring or synthetic hydrocarbon composed of linked repeating organic subunits that lack charged groups. It may be linear, dominantly linear with some branching, or dominantly branched. Examples suitable to practice the methods include but are not limited to polyethylene glycol (PEG), polypropylene glycol, polyvinylpyrrolidone (PVP), and others. PEG has a structural formula $HO-(CH_2-CH_2-O)_n-H$. Examples include, but are not limited to compositions with an average polymer molecular weight less than 500 Daltons.

"Protein-precipitating salt" or "antibody-precipitating salt" or "IgG-precipitating salt" refers to a salt that embodies the ability to mediate precipitation of a desired protein. Common examples include sodium or ammonium sulfate, sodium or potassium citrate, sodium or potassium phosphate. Such salts are commonly referred to as kosmotropic salts.

"Non-protein-precipitating salt" or "non-antibody-precipitating salt" or "non-IgG-precipitating salt" refers to a salt that lacks the ability to mediate precipitation of a desired protein, and may embody the ability to increase solubility of a desired protein. Common examples include but are not limited to sodium or potassium chloride, sodium or potassium acetate, sodium or potassium thiocyantate, or guanidinium chloride. Some such salts are commonly referred to as chaotropic salts, while others are neither referred to as chaotropic nor kosmotropic.

"Polynucleotide" refers to a biopolymer composed of multiple nucleotide monomers covalently bonded in a chain. DNA (deoxyribonucleic acid) and RNA (ribonucleic acid) are examples of polynucleotides. Polynucleotides can have a high propensity for formation of hydrogen bonds.

"Protein preparation" refers to any aqueous or mostly aqueous solution containing a protein of interest, such as a cell-containing cell culture harvest, a (substantially) cell-free cell culture supernatant, or a solution containing the protein of interest from a stage of purification.

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope.

"Void exclusion" refers to a chemical interaction by which at least one component of a sample inside the environment of a column packed with electrostatically charged particles is constrained to reside substantially within the interparticle space of the column bed as a result of being electrostatically repelled and/or unable to overcome physical resistance to pore entry that may be imposed either by the inherent dimension of the pores residing in the particles, or imposed secondarily by the physical format in which electrostatic charges are presented within the pores.

"Void exclusion mode" or "void exclusion chromatography" refers to a fractionation method practiced in columns of packed electrostatically charged particles, whereby the sample volume applied to the column is not greater than the interparticle volume within the packed bed, and a desired sample component, such as a protein, is unable to enter the pores of the particles, and is thereby constrained to travel through the interparticle space, which is also known commonly as the void volume. A fundamental and distinctive feature of void exclusion chromatography is that the sample need not be equilibrated to the column operating conditions, as a result of which the sample conditions may include extremely high salt concentrations and pH values considered unsuitable for conducting chromatography on electrostatically charged particles. Further fundamental and distinctive features include its unique ability to achieve buffer exchange in conjunction with fractionation. In void exclusion chromatography, the desired protein elutes in the buffer to which the column is equilibrated, independent of the sample composition in which it was applied to the column.

In certain embodiments, the sample is contacted with the solid allantoin for at least about fifteen minutes prior to the step of separating the solid from the liquid fraction. In certain other embodiments, the sample is incubated with the solid for less than 15 minutes or from about 15-30 minutes, or more than 30 minutes or about 60 minutes or more than about 60 minutes. As a general matter, the binding of most large biological targets with allantoin appears to be essentially instantaneous, and achieves completion in less time than a removal step can be conducted. Prudent laboratory practice nevertheless recommends that incubation time be evaluated systematically, and even if it turns out not to have a substantial effect for a particular application, a consistent treatment time should be specified and adhered to for a particular application.

A useful starting point in applying the methods disclosed herein is to simply add allantoin in an amount of 10% w/v to the protein preparation containing the desired protein. No alteration of sample conditions is required. Experimental evidence suggests that reaction between endotoxin and insoluble allantoin is essentially instantaneous and achieves its highest level in less time than would be required for the fastest practical subsequent removal of solids. Incubation time therefore seems not to be a significant practical consideration, thus this step may be conducted with whatever incubation time is most convenient. Nevertheless, prudent laboratory practice suggests that a consistent time interval be observed to maximize reproducibility among experiments. Experiments intended to optimize the degree of endotoxin removal from multiple samples of a particular desired protein that may be produced on a regular or routine basis may optionally involve adjusting the proportion of allantoin to a higher or lower supersaturating concentration, and/or adjusting the pH of the preparation, or its content of salts or other components. Even though such adjustments may not affect the interaction between allantoin and endotoxin, they may affect the interaction between endotoxin and the desired protein, which may have a substantial influence on the ability of the present technology, or any other, to achieve the desired reduction of endotoxin. Preliminary data indicate that product recovery may be inversely proportional to the amount of allantoin present, so it may be advantageous to determine the minimum amount of allantoin to achieve the best effect. Experimental data also indicate that this effect is more pronounced with larger proteins, so smaller proteins are most likely to support high recovery despite very high concentrations of allantoin. One skilled in the art will appreciate that the methods described herein can be carried out with substantially higher allantoin concentrations than 10%, such as 20%, or 30%, or 40%, or 50%, or higher. The costs efficiency of performing the methods in this manner may diminish, but this may be tolerable given that allantoin is a relatively inexpensive commodity.

Removal of solids from the allantoin treated protein preparation may be performed by any convenient means, including filtration, centrifugation, a combination of centrifugation and filtration, or other means. The means of removing solids has no effect on the performance of the methods disclosed herein so long as care is taken not to introduce additional sources of endotoxin.

The electropositive void exclusion step imposes no requirement for equilibration of the protein preparation, and can accommodate any protein preparation from which solids have been removed. The electropositive void exclusion step does however determine the volume of sample that can be treated in a single cycle, since the volume of sample applied to the electropositive void exclusion column must be no greater than the interparticle volume of the column containing the electropositive void exclusion chromatography media. In a gravity settled column, the interparticle volume of such a column generally consists of about 40% of the volume of the gravity-settled bed. Axial compression of the media should be avoided since it will reduce the interparticle volume and in turn the volume of sample that can be applied to a particular electropositive void exclusion column. A chromatography medium known as UNOsphere Q (Bio-Rad) provides a convenient option to begin with, since it supports the highest void exclusion efficiency observed to date, though others can be evaluated if desired. Since the void exclusion step has a particular dependency on the volume of the applied sample, it is important that the sample be applied in a manner that affords the least possible opportunity for the sample to be diluted on its way to the column, since this would be understood to increase the volume of the sample entering the column. If the volume of sample entering the column exceeds the interparticle volume, endotoxin removal efficiency may be compromised. One way to minimize sample dilution leading to excess sample volume is to apply the sample through a so-called superloop. Another way is to use columns designed to permit the fluid level to spontaneously descend to the top of the bed, add the sample and let it enter the column until it has fully entered, then apply buffer to impel the sample through the column. The most effective application of the void exclusion step will require development of appropriate column equilibration buffer conditions in some cases. Such conditions will be dependent on the properties of the desired protein to be applied. In the case of alkaline proteins such as many IgG monoclonal antibodies, Fab, and F(ab')$_2$ fragments derived from such antibodies, a convenient starting formulation for the equilibration buffer may be 50 mM Tris, pH 8.0. If recovery of the desired protein less than 98%, then a series of experiments in which NaCl concentration is increased in increments of 50 mM may be evaluated. Further optimization may be conducted in smaller increments. As a general matter, the lowest salt concentration that supports adequate recovery of the desired protein will achieve the greatest reduction of endotoxin. pH may be varied experimentally. Experimental data show that electropositive void exclusion of some IgG monoclonal antibodies in 50 mM Tris, pH 8.0 additionally achieves greater than 99% reduction of non-antibody proteins. In the case of non-IgG proteins, a convenient equilibration buffer to start with is 50 mM Hepes, pH 7.0. As with IgG, recovery or less than 98% suggests that better performance may be obtained from increasing the salt concentration, or adjusting pH. It will generally be more convenient to use a running buffer with the same formulation as the column equilibration buffer, but a different buffer may be used for the running buffer. Where the running buffer is different from the equilibration buffer, it may be of any formulation that does not damage the column since it will not affect the ability of the methods to reduce endotoxin. Experiments conducted to optimize the formulation of the electropositive void exclusion equilibration buffer may employ samples considerably smaller than the maximum volumetric capacity of a given column, such as 20%, or 10%, or 5%, or 1% to minimize expenditure of the desired protein. Depending on the formulation of the equilibration buffer, the greatest reduction of endotoxin may be observed at the allantoin affinity step or the electropositive void exclusion step. In some cases the relative contribution of the more effective step may be highly dominant. A linear flow rate of about 200 cm/hr is a reasonable flow rate for operating the electropositive void exclusion step. Lower flow rates may produce better results but increase the process time. Higher flow rates may produce acceptable results and reduce the process time. One skilled in the art will appreciate that the methods described herein can be carried out at substantially higher flow rates than 200 cm/hr, but the loss of performance from doing so may be unacceptable.

It will be apparent to the person of skill in the art that it may be advantageous to sanitize the electropositive void exclusion column and associated hardware with 1 M sodium hydroxide prior to use to minimize the possibility that it may contribute to the endotoxin. For the same reason, it may be advantageous to make a special effort during the preparation of buffers to minimize their endotoxin content. One practice towards this goal is to filter all buffers through a membrane with a pore size cutoff corresponding with globular compounds with a molecular mass of less than about 10 kDa. Another approach, for buffers lacking calcium or phosphate, is to add hydroxyapatite to the buffer in an amount of about 0.1-0.2% before filtration through a 0.22 or 0.45 micron membrane. In all cases, vessels used to practice the methods are ideally endotoxin free so far as reasonably possible. Given the labor involved with washing a complex chromatograph to eliminate sources of endotoxin contamination, it will be apparent that the availability of free standing kits will be highly advantageous.

EXAMPLES

Example 1

Endotoxin reduction from an IgG-endotoxin mixture by combination of allantoin and void exclusion chromatography. Endotoxin was added to 1 mg/mL human IgG (clone her2) in 20 mM Hepes, 150 mM NaCl, pH 7.5 to 3,300 EU/ml. 30% (w/v) allantoin was added to aliquots of this mixture and allowed to mix for 15 minutes at room temperature. The suspension was clarified by centrifugation. Protein recovery was more than 50% and the endotoxin content of the supernatant was reduced by more than 99% to less than 20 EU/ml. 1 mL of IgG containing supernatant was then applied to a 8.8 mL gravity column packed with electropositive porous particles (UNOsphere Q, Bio-Rad Laboratories) equilibrated with 20 mM Hepes, 150 mM NaCl, pH 7.5. Next, 15 ml of equilibration buffer was applied and 1 ml fractions were collected at the outlet of the column. Elution fractions were analysed by UV absorbance at 280 nm and 254 nm and by an LAL kinetic chromogenic endotoxin assay. More than 90% of the IgG eluted in the combined fractions 4, 5 and 6 (i.e. elution volume from 3 to 6 ml), whereas soluble allantoin only eluted from fraction 7 onwards. Void exclusion chromatography further reduced the endotoxin levels in the combined fractions 4, 5 and 6 by more than 95%. The overall endotoxin reduction by combination of allantoin-mediated co-precipitation and electropositive void exclusion chromatography was more than 99.95% to less than 1 EU/ml. In a related experiment differing only by the void exclusion column being equilibrated to 50 mM Tris, pH 8.2, the combined result of allantoin-void exclusion treatment was a reduction of endotoxin to less than 0.01 EU per mL.

Example 2

Endotoxin reduction from an IgG-endotoxin mixture by void exclusion alone. Endotoxin was added to 1 mg/mL human IgG (clone her2) in 20 mM, Hepes 150 mM, NaCl pH 7.5 to 400 EU/ml. The sample was subjected to void exclusion under the same conditions as described in example 1. About 90% of the IgG eluted in the combined fractions 4, 5 and 6 and endotoxin content was reduced by 99.6%.

Example 3

Endotoxin reduction from a protein solution by combination of allantoin-mediated co-precipitation and void exclusion chromatography. Endotoxin was added to a sample of 1 mg/ml bovine serum albumin (BSA) in 20 mM Hepes 350 mM NaCl pH 7.5. The sample was treated as in example 1, except that the equilibration and elution buffer used for electropositive void exclusion chromatography contained 350 mM NaCl. Allantoin-mediated co-precipitation reduced endotoxin by more than 99.95% with more than 90% protein recovery. Void exclusion chromatography did not achieve further reduction of endotoxin, but it effectively removed soluble allantoin from the protein sample with more than 85% protein recovery.

Example 4

Effect of salt on endotoxin-removal by allantoin-mediated co-precipitation. Allantoin (30% w/v) was added to an aqueous solution of 20 mM HEPES, pH 7.5 containing 10,000 EU/ml. Salt concentrations were chosen at 0, 0.05, 0.15, 0.5 and 2 M NaCl. The endotoxin removal efficiency of allantoin at 0 M NaCl was more than 99.99% and was independent of salt concentrations up to 0.5 M NaCl. At 2 M NaCl, the endotoxin removal efficiency of allantoin increased to 99.997%.

Example 5

Effect of pH on endotoxin-removal by allantoin-mediated co-precipitation. The experiment in Example 4 was repeated at 150 mM NaCl and pH values of 3.5, 5.5, 7.5 and 9.5. Endotoxin removal was more than 99.9% at all pH values, and was highest at pH 7.5 (99.99%).

Example 6

Effect of surfactant on endotoxin-removal by allantoin-mediated co-precipitation. The experiment described Example 4 was repeated at 150 mM NaCl in the presence of detergent (0.1-10% Tween 20). The endotoxin removal efficiency of allantoin slightly decreased in the presence of detergent, but was consistently higher than 99.8%.

Example 7

Effect of salt on endotoxin-removal by void exclusion chromatography. 1 ml of an aqueous solution of 20 mM HEPES, pH 7.5 containing about 1,000 EU/ml was applied to a 8.8 mL gravity column packed with electropositive porous particles (UNOsphere Q, Bio-Rad Laboratories) as described in Example 1. Salt concentrations of the sample, equilibration and elution buffers were chosen at 150, 250 and 350 mM NaCl. Endotoxin-reduction by void exclusion was 35% at 350 mM NaCl and 99.99% at 250 mM NaCl. At 150 mM NaCl, electropositive void exclusion reduced the endotoxin levels of all elution fractions below the detection limit (<0.01 EU/ml).

Example 8

Effect of pH on endotoxin-removal by electropositive void exclusion chromatography. The experiment in Example 7 was repeated at 150 mM NaCl at pH 3.5, 5.5 and 7.5. Electropositive void exclusion chromatography reduced the endotoxin levels of all elution fractions below the detection limit (<0.01 EU/ml) over the entire pH range.

Example 9

Effect of organic additives in combination with allantoin. Cell-containing cell culture harvest containing a monoclonal IgG was treated with 1% allantoin in combination with 0.01% ethacridine. The sample, at a pH of about 7.2 and a conductivity of about 13.5 mS, these conditions corresponding with so-called physiological conditions, was passed over a column packed chromatography media including equal amounts of the metal affinity ligand TREN (BioWorks TREN hi-sub) and a hydrophobic ligands (Macroprep T-butyl). Antibody recovery following the previous steps was 99%. The sample was applied to a void exclusion column packed with UNOsphere Q. Recovery from the electropositive void exclusion step was 99%, corresponding to an overall recovery of 98%. Endotoxin content was less than 1 EU/mL, greater than 99% of host protein contaminants were removed and DNA was reduced by more than 6 logs. Combined virus reduction was greater than 76%. This example illustrates that the allantoin affinity and electropositive void exclusion steps may be separated by one or more steps; the allantoin step may be conducted effectively in the presence of organic modifiers; and the methods disclosed herein may have the additional benefit of removing a range of contaminants beyond endotoxins.

Example 10

Electropositive void exclusion-qualified chromatography media. Various commercial anion exchange chromatography media were evaluated for their ability to conduct electropositive void exclusion chromatography. UNOsphere Q and Nuvia Q achieved acceptable exclusion of an experimental IgG monoclonal antibody to the void volume. Capto Q was less effective but marginally effective. Other anion exchangers achieved much lower efficiency, including GigaCap Q, Tentacle DEAE-Fractogel, Dowex Ag1x4, Q Sephadex A25, Q Sepharose Fast Flow, and POROS HQ. Monolithic and membrane exchangers were completely unsuitable. These results illustrate that not all anion exchangers are electropositive void exclusion-capable. Though candidates beyond UNOsphere Q and Nuvia Q may be suitable, these media provide a convenient place to start.

Example 11

Void exclusion chromatography with multimodal hydrophobic interaction-hydrogen bonding-electropositive chromatography particles. A column was prepared containing Capto adhere, a chromatography medium purported to embody anion exchange, hydrogen bonding, and hydrophobic interaction functionalities. Because of its chemical functionalities beyond simple electropositivity, and cooperative interactions among those functionalities with proteins introduced into the column, antibodies tend to bind over a broader range of conditions than they do on media marketed for the technique of anion exchange chromatography, which means that the conditions under which electropositive void exclusion can be conducted are proportionally narrowed. Experiments with various concentrations of NaCl and various pH values identified 50 mM acetate, pH 5.0 as suitable for mediating void exclusion of the applied antibody. Under these conditions, Capto adhere achieved about 10-fold greater endotoxin reduction than UNOsphere Q.

Example 12

A sample of purified IgG containing 22.8 endotoxin units per mL after treatment with 5% allantoin was further processed by anion exchange chromatography in void exclusion mode on UNOsphere Q to eliminate excess allantoin and further reduce endotoxin levels. In one experiment where the column was equilibrated with 50 mM Hepes, 150 mM NaCl, pH 7.0, endotoxin was reduced to 0.472 EU/mL. In another experiment where the column was equilibrated with 50 mM Hepes, 100 mM NaCl, pH 7.0, endotoxin was reduced to 0.078 EU/mL. In another experiment where the column was equilibrated with 50 mM Hepes, 50 mM NaCl, pH 7.0, endotoxin was reduced to 0.022 EU/mL.

It will be apparent that the methods disclosed herein can be practiced over a wide range of scales, from the treatment of sample volumes less than 1 mL to hundreds or even thousands of liters. It is within the ability of persons of ordinary skill in the art, on the basis of the information provided herein, to adjust the scale of any particular application to any level required to enjoy the greatest benefits of the methods disclosed herein.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present methods.

Many modifications and variations of the methods can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the embodiments disclosed herein being indicated by the following claims.

What is claimed is:

1. A method comprising: (i) adding allantoin in a supersaturating amount to a protein preparation comprising a desired protein and an amount of at least one endotoxin as a contaminant; (ii) removing solids from the protein preparation to provide a sample for further purification by void exclusion chromatography using a packed particle bed of electropositive particles in a column, the packed particle bed having an interparticle volume; (iii) applying a sample volume of the sample to the packed particle bed, wherein the electropositive particles support void exclusion chromatography, and wherein the sample volume is not greater than the interparticle volume, and (iv) eluting a purified sample comprising the desired protein and a reduced amount of the at least one endotoxin, wherein the eluted desired protein resides in a buffer to which the column was equilibrated, independently from a buffer content of the sample applied to the column.

2. The method of claim 1, wherein the supersaturating amount of allantoin comprises an amount selected from the group consisting of: (i) about 10%, (ii) about 5%, (ii) from about 0.6 to about 6%, (iii) from about 6% to about 10%, (iv) from about 10% to about 15%, (v) from about 15 to about 20%, (vi) from about 20 to about 50%, and (vii) greater than 50%, wherein the amount is provided as weight/volume.

3. The method of claim 1, wherein removing the solids comprises one selected from the group consisting of sedimentation, centrifugation, filtration, and combinations thereof.

4. The method of claim 1, wherein a pH or salt concentration of the protein preparation is adjusted before, during, or after the adding step.

5. The method of claim 1, wherein a pH or salt concentration of the protein preparation is adjusted before the applying step.

6. The method of claim 1, wherein the sample volume is less than the interparticle volume of the packed particle bed such that the sample volume relative to the packed bed is one selected from the group consisting of:
(i) less than about 40%, (ii) less than about 35%, (iii) less than about 30%, (iv) less than about 20%, (v) less than about 10%, (vi) less than about 5%, (vii) less than about 2%, and (viii) less than about 1%.

7. The method of claim 1, wherein the sample volume applied to the bed is less than the interparticle volume by an increment consisting of one selected from the group of 99% of the interparticle volume, 95% of the interparticle volume, 90% of the interparticle volume, 80% of the interparticle volume, 70% of the interparticle volume, 60% of the interparticle volume, 50% of the interparticle volume, 25% of the interparticle volume, 10% of the interparticle volume, 5% of the interparticle volume, 2% of the interparticle volume, 1% of the interparticle volume, and intermediate volume percent thereof.

8. The method of claim 1, wherein the packed particle bed comprises an anion exchange media and before the applying step, the method further comprises equilibrating the packed particle bed of the anion exchange media with the buffer, wherein the buffer is selected to prevent the desired protein from substantially binding to the anion exchange media.

9. The method of claim 8, wherein preventing the desired protein from substantially binding to the anion exchange media comprises providing the buffer having a sufficiently low pH.

10. The method of claim 8, wherein preventing the desired protein from substantially binding to the anion exchange media comprises providing the buffer having a sufficiently high salt concentration.

11. The method of claim 9, wherein the buffer has a pH comprising one selected from the group consisting of (i) about 7, (ii) about 8, (iii) about 6, and (iv) a range from about 6 to about 8.

12. The method of claim 9, wherein the buffer comprises a sodium chloride concentration comprising one selected from the group consisting of (i) about 0 mM, (ii) about 50 mM, (iii) about 150 mM, and (iv) a range from about 0 mM to about 150 mM.

13. The method of claim 1, wherein the electropositive particles comprise an anion exchange chromatography media comprising a positively charged quaternary amine.

14. The method of claim 1, wherein the applying of (iii) and/or the eluting of (iv) is performed at a linear flow rate comprising a non-zero linear flow rate selected from the group consisting of (i) about 300 cm/hr or less, (ii) about 200 cm/hr or less, (iii) about 100 cm/hr or less, and (iv) about 50 cm/hr or less.

15. The method of claim 1, wherein the reduced amount of the at least one endotoxin in the purified sample is an amount reduced by 99% or more compared to the amount of the at least one endotoxin in (i), or is an amount less than 1 EU/ml.

16. A method comprising: (i) providing a sample comprising a protein preparation comprising a desired protein and an amount of endotoxin, the sample having a sample volume and being suitable for void exclusion chromatography on a packed particle bed of electropositive particles in a column, wherein the electropositive particles support void exclusion chromatography, the packed particle bed having an interparticle volume, and wherein the sample volume is not greater than the interparticle volume; (ii) applying the sample to the packed particle bed, and (iii) eluting a purified sample comprising the desired protein and a reduced amount of the endotoxin.

17. The method of claim 16, wherein the reduced amount of endotoxin is an amount reduced by 99% or more compared to the amount of endotoxin in (i), or is an amount less than 1 EU/ml.

18. The method of claim 1 or 16, wherein the desired protein comprises an antibody or an antibody fragment.

* * * * *